US008079265B2

(12) United States Patent
Brignac et al.

(10) Patent No.: US 8,079,265 B2
(45) Date of Patent: Dec. 20, 2011

(54) PORTABLE SCANNER DEVICE FOR METALLURGICAL, NONDESTRUCTIVE TESTING

(75) Inventors: Jacques L. Brignac, Simsbury, CT (US); Roland R. Moser, Zurich (CH)

(73) Assignee: Alstom Technology Ltd (CH)

( * ) Notice: Subject to any disclaimer, the term of this patent is extended or adjusted under 35 U.S.C. 154(b) by 1179 days.

(21) Appl. No.: 11/829,208

(22) Filed: Jul. 27, 2007

(65) Prior Publication Data

US 2009/0027736 A1 Jan. 29, 2009

(51) Int. Cl.
*G01N 29/26* (2006.01)
(52) U.S. Cl. .................. 73/627; 73/618; 73/634
(58) Field of Classification Search .......... 73/627, 73/618–622, 629, 634
See application file for complete search history.

(56) References Cited

U.S. PATENT DOCUMENTS

| | | | |
|---|---|---|---|
| 2,742,259 A | 4/1956 | Boucher | |
| 4,006,359 A | 2/1977 | Sullins et al. | |
| 5,311,785 A * | 5/1994 | Bar-Shay | 73/866.5 |
| 5,359,898 A | 11/1994 | Latimer | |
| 5,404,755 A | 4/1995 | Olson et al. | |
| 5,454,267 A | 10/1995 | Moreau | |
| 5,476,010 A | 12/1995 | Fleming et al. | |
| 5,549,004 A * | 8/1996 | Nugent | 73/622 |
| 5,782,769 A | 7/1998 | Hwang et al. | |
| 6,220,099 B1 * | 4/2001 | Marti et al. | 73/633 |
| 6,271,670 B1 | 8/2001 | Caffey | |
| 6,282,964 B1 | 9/2001 | Hancock | |
| 6,373,914 B1 | 8/2002 | Gill | |
| 6,502,452 B1 | 1/2003 | Gill | |
| 6,567,795 B2 | 5/2003 | Alouani | |
| 6,799,466 B2 | 10/2004 | Chinn | |
| 6,920,792 B2 | 7/2005 | Flora | |
| 7,444,876 B2 * | 11/2008 | Sarr et al. | 73/618 |
| 7,617,732 B2 * | 11/2009 | Bui et al. | 73/618 |
| 7,640,811 B2 * | 1/2010 | Kennedy et al. | 73/634 |
| 7,817,845 B2 * | 10/2010 | Suh et al. | 382/141 |
| 2003/0188589 A1 | 10/2003 | Harthorn et al. | |

FOREIGN PATENT DOCUMENTS

| | | |
|---|---|---|
| DE | 19529782 | 2/1997 |
| EP | 0378480 | 10/1990 |
| WO | WO 94/01766 | 1/1994 |
| WO | WO 99/41600 | 8/1999 |

OTHER PUBLICATIONS

Harfang Microtechniques Inc. [online]; [retrieved on Sep. 2006]; retrieved from the internet http://www.harfangmicro.com, Boiler Tube Imaging, 2p, Quebec, Que-Canada.

(Continued)

*Primary Examiner* — J M Saint Surin
(74) *Attorney, Agent, or Firm* — Cantor Colburn LLP

(57) ABSTRACT

A portable, self-contained scanner device for metallurgical, nondestructive testing is provided. The portable, self-contained scanner device includes a chassis having wheels extending beneath a lower surface thereof, a nondestructive testing probe detachably fixed to the chassis, and a computer processor device coupled to the chassis. The computer processor device includes applications executable by the computer processor device for performing the metallurgical, nondestructive testing on a test subject. The scanner device also includes a display device that displays images in response to the metallurgical, nondestructive testing. The chassis, computer processor device, and display device move along the test subject as a single unit.

19 Claims, 3 Drawing Sheets

OTHER PUBLICATIONS

Russell NDE Systems Inc., [online]; [retrieved 2007]; retrieved from the internet http://www.russelltech.com/ut/DarisMain.html, 2007, An Innovation in Tube Inspection DARIS,1p, Edmonton, Alberta, Canada.

Wikipedia. [online]; [retrieved on Apr. 13. 2007]; retrieved from the Internet http://en.wikipedia.org/wiki/Internal_Rotary_Inspection_System, Internal rotary inspection system 1p.

NDT, [online]; [retrieved on Apr. 13, 2007]; retrieved from the Internet http://www.ndt.net/apcndt2001/papers/7/7/htm Charles Panos, Condition Monitoring-Process Plant Tube Inspection and Ongoing Commitment by Plant Owners and Operators,10p, International Tube Testing Pty Ltd, Qld, Australia.

PCT International Search Report and The Written Opinion of the International Searching Authority dated Oct. 17, 2008—(PCT/US2008/069720).

* cited by examiner

PORTABLE SCANNER DEVICE FOR METALLURGICAL, NONDESTRUCTIVE TESTING

TECHNICAL FIELD

The present disclosure relates generally to a scanner device, and more particularly, to a portable, self-contained scanner device for metallurgical, nondestructive testing.

BACKGROUND

Testing of pressure parts and large diameter tubes or piping (e.g., where the diameter is greater than 300 mm) using non-destructive testing techniques is an arduous task, particularly when testing girth and seam welds. For example, the parts to be measured are oftentimes installed in areas that require compact handheld equipment that the testing personnel operate by hand. Fully automated or semi-automated testing equipment can be bulky and too cumbersome for installation in these inaccessible areas. Further, using advanced handheld equipment (e.g., hand-guided scanners), the sensors (e.g., time of flight diffraction sensors, phased array, electromagnetic acoustic transducers, etc.) are mounted on the scanner and the data acquisition units, as well as the display unit, are both physically separate from the scanner and linked together via cabling. As a result, oftentimes two operators are needed to conduct the testing: one tester that guides the scanner, and another tester that observes the data acquisition process. If using only one operator, the data acquisition component and data display unit would need to be in the same location for simultaneous scanning and observation of the data. However, when testing in a confined space, e.g., boiler equipment, this may not be possible.

What is needed, therefore, is a compact, self-contained scanning device that enables a single operator to conduct both the testing and the data acquisition and observation activities with respect to a metallurgical, nondestructive test.

SUMMARY

According to the aspects illustrated herein, there is provided a portable, self-contained scanner device for metallurgical, nondestructive testing. The portable, self-contained scanner device includes a chassis having wheels extending beneath a lower surface thereof, a non-destructive testing probe detachably fixed to the chassis, and a computer processor device coupled to the chassis. The computer processor device includes applications executable by the computer processor device for performing the metallurgical, nondestructive testing on a test subject. The scanner device also includes a display device that displays images in response to the metallurgical, nondestructive testing. The chassis, computer processor device, and display device move along the test subject as a single unit.

According to the other aspects illustrated herein, a chassis for a metallurgical nondestructive scanner device is provided. The chassis includes a base, sidewalls extending upward from the base, and an opening formed by the base and the sidewalls for receiving a computer processor device. The chassis also includes wheels extending beneath the base of the chassis, at least one nondestructive testing probe fixed to the chassis, and an interface connector attached to the chassis. The interface connector is communicatively coupled to the at least one probe. The interface connector is configured to connect to a communications port of the computer processor device.

The above described and other features are exemplified by the following figures and detailed description.

BRIEF DESCRIPTION OF THE DRAWINGS

Referring now to the Figures, which are exemplary embodiments, and wherein the like elements are numbered alike.

DETAILED DESCRIPTION

A portable, self-contained scanner device for metallurgical, nondestructive testing is provided in accordance with exemplary embodiments. The self-contained scanner device is compact and usable in conjunction with various sensors. The scanner device is self-contained, such that its collective components move along a test subject as a single unit. As a result of its self-contained configuration, one tester alone may bring the scanner device into confined spaces and simultaneously guide the scanner device and collect and observe test data via a display mounted thereon.

Figure 1:
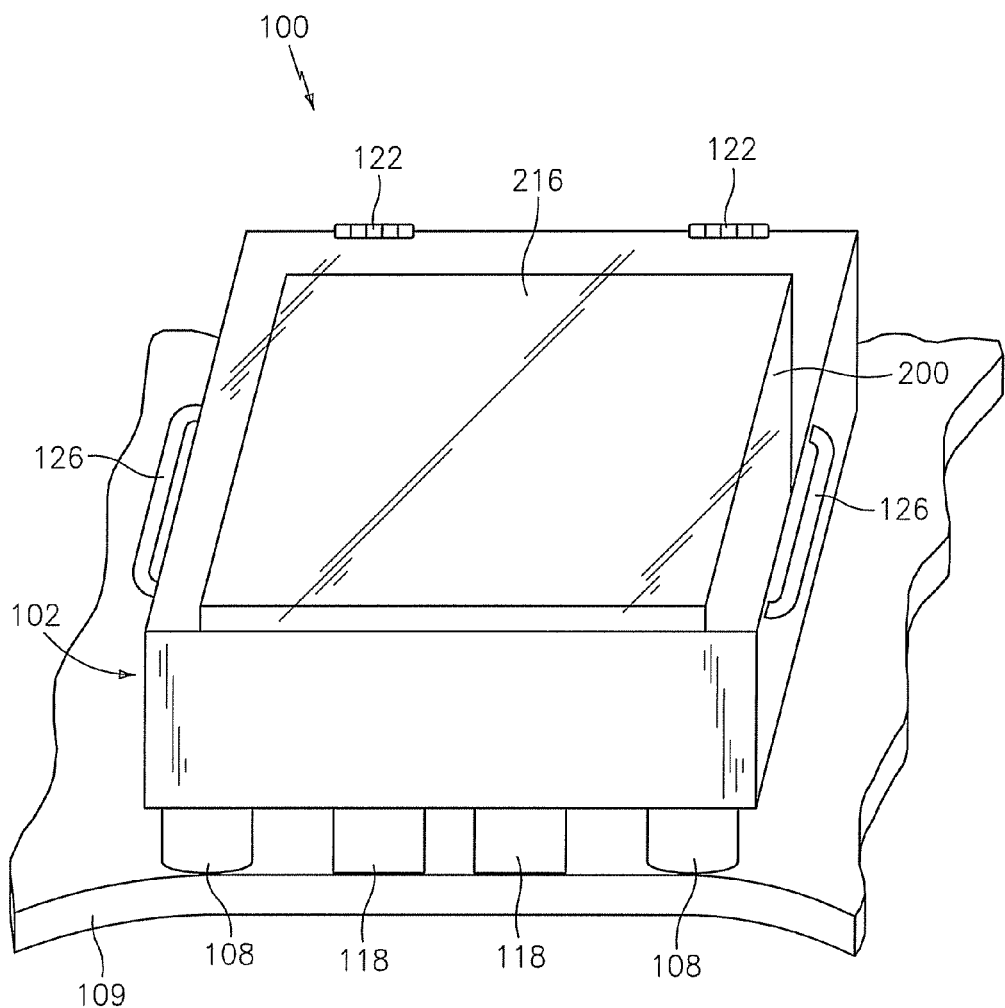
FIG. 1 is a perspective view of a scanner device including a chassis and computer processor device in an exemplary embodiment.
Figure 2:
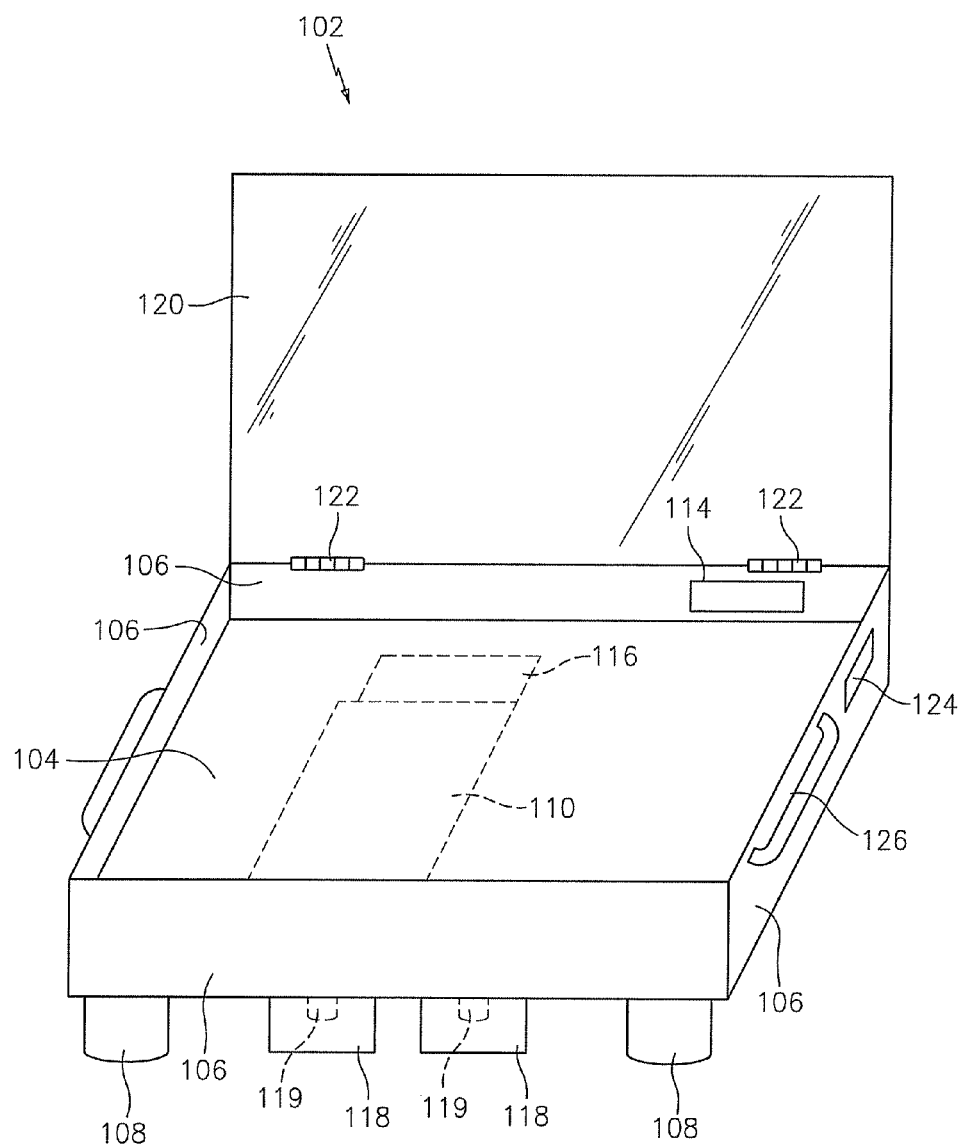
FIG. 2 is a perspective view of the chassis illustrated in FIG. 1.
Figure 3:
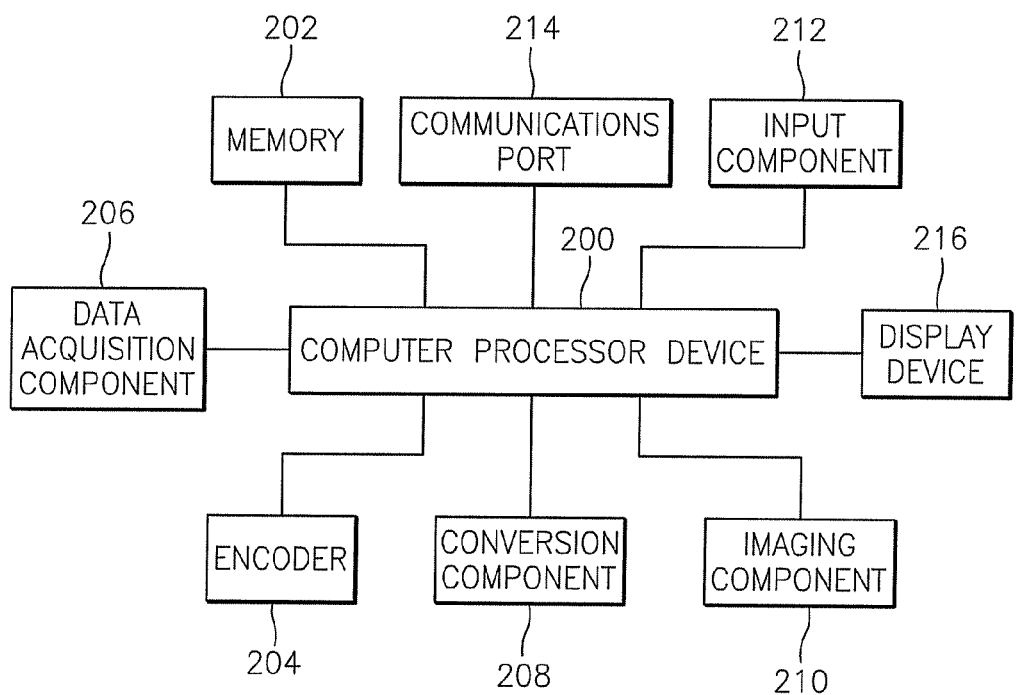
FIG. 3 is a block diagram illustrating the computer processor device of FIG. 1.

Turning now to FIGS. 1-3, a portable, self-contained scanner device for metallurgical, nondestructive testing will now be described in accordance with exemplary embodiments. The portable, self-contained scanner device 100 includes a chassis 102 and a computer processor device 200 coupled to the chassis 102. In one exemplary embodiment, the chassis 102 includes a base 104, sidewalls 106 extending upward from the edges of the base 104, and an opening formed by the base and the sidewalls. The computer processor device 200 is then disposed in the opening of the chassis 102. It will be understood, however, that other configurations may be employed for the chassis 102 in order to realize the advantages of the invention.

The chassis 102 also includes at least one probe 118 detachably fixed to a lower surface of the chassis 102 (e.g., at the base 104 thereof). It is also contemplated that the probe 118 is detachably fixed to a sidewall 106 of the chassis and arranged such that the probe 118 extends beneath the lower surface of the chassis 102. The probe 118 may be an ultrasonic transducer, electromagnetic acoustic transducer, or any other probe useful for metallurgical, nondestructive testing. The chassis 102 also includes an interface connector 114 attached to the chassis 102. The interface connector 114 is communicatively coupled to the probe 118 by wiring, printed circuit board, or the like. The interface connector 114 may be a small computer systems interface (SCSI) connector.

The scanner device 100 also includes a display device 216 that displays images in response to the testing. The images are viewable by a tester during operation of the scanner device 100. The display device 216 will be described further herein.

The computer processor device 200 includes a communications (input/output) port 214 coupled to the interface connector 114 for enabling communications between the probe 118 installed on the chassis 102 and the computer processor device 200. In exemplary embodiments, the computer processor device 200 also includes software applications (instructions) executable by the computer processor device 200 for performing metallurgical nondestructive testing on a test subject 109. The test subject 109 may be a pipe or tube, and the testing may include measuring the girth and/or integrity of seam welds on the pipe or tube. The probe 118 receives commands from at least one of the applications via the communications port 214 and the interface connector 114, and transmits a test signal (e.g., ultrasonic pulse, acoustic wave, etc.) to the test subject 109 in response to the command. The probe 118 senses a response to the test signal from the test subject 109 and, in turn, provides a response signal to the computer processor device 200.

The applications executable by the computer processor device 200 may include a data acquisition component 206 that receives response signals resulting from test signal emission by the probe 118, an encoder 204 for determining a position of the scanner device 100 on the test subject 109, and defining a position location on the test subject 109 at which the response signals are acquired, a data conversion component 208 for digitizing or otherwise processing the response signals, and an imaging component 210 for presenting processed response signals on the display device 216. The type of probe 118 employed and the type of data acquisition components 206 used in the scanner device 100 depend upon the nature of testing to be conducted (e.g., time of flight diffraction ultrasonics, phased array ultrasonics, electromagnetic acoustic wave, etc.).

The computer processor device 200 may also include memory 202 for storing the applications executable by the computer processor device 200, as well as other data, such as response signals and other test results.

In one exemplary embodiment, the computer processor device 200 is integrally formed with the chassis 102 as a single unit. In an alternative exemplary embodiment, the computer processor device 200 and chassis 102 are separable, such that the computer processor device 200 and chassis 102 may be easily separated after testing is completed. In this alternative exemplary embodiment, the computer processor device 200 is coupled to the chassis 102 (e.g., disposed in the chassis 102) and is detachably fixed to the chassis 102 via the interface connector 114 and the communications port 214. In addition, resilient material (e.g., foam), straps, and/or other securing means may be installed within the chassis 102 to prevent damage to the computer processor device 200 during handling of the scanner device 100. In addition, the computer processor device 200 may be removed from the chassis 102 by opening a cover 120 of the chassis 102 as described further herein.

If the chassis 102 and the computer processor device 200 are separate units (i.e., not integrally formed), the chassis 102 may be configured, e.g., to accept commercially available tablet computers for use as the computer processor device 200, which allows the display device 216 thereof to face outwards (i.e., with the display device 216 under the cover 120, which may be entirely or partially transparent, and facing the operator) and includes touch-screen capability. As used herein, a "tablet computer" is a notebook, laptop or slate-shaped mobile computer having a touch-sensitive display screen that allows the user to operate the computer with a stylus, digital pen, or a fingertip, instead of, or in addition to, a keyboard or mouse. Tablet computers include so-called convertible notebooks, which have a base body with an attached keyboard, wherein the base attaches to the display at a single joint called a swivel hinge or rotating hinge. The joint allows the screen to rotate around 180° and fold down on top of the keyboard to provide a flat writing surface.

With standard input/output ports, the scanner device 100 may allow any commercially available tablet computer to be used, and the cover 120 allows viewing of the display device 216 while providing protection to the tablet computer. The touch screen facilitates operation of the scanner device 100. Thus configured, the tablet computer can be installed in the chassis 102 to acquire data and then be removed from the chassis 102 for data analysis and/or for data upload to a network. The tablet computer need not be a costly application-specific computer dedicated for use with the scanner device 100. It only needs the appropriate software.

Additionally, a second display device may be communicatively coupled to the computer processor device 200 to facilitate testing. For example, eyewear that includes display capabilities may be worn by the tester during operation of the scanner device 100. The eyewear may be wireless (e.g., in communication with the chassis using short-range radio waves, such as Bluetooth™), or may be physically connected to the chassis via cabling.

In an exemplary embodiment, the chassis 102 may further include tool posts 119 for supporting each of the probes 118. The posts 119 may be connected to the lower surface of the chassis 102 (e.g., at a base 104 thereof) and may be positioned between the lower surface of the base 104 and the probes 118. Alternatively, the posts 119 may be attached to a sidewall 106 of the chassis and arranged such that the probe 118 extends downward, beneath the lower surface of the chassis 102. In addition, the posts may include a spring-loaded mechanism to force the probes toward the test subject 109 for applying probe pressure on the test subject 109. The posts 119 allow the probes 118 to be removed from the chassis 102 and replaced with different probes 118. As a result, the same chassis 102 can be used to conduct different forms of metallurgical testing by simply changing the probes 118 and any required applications within the computer processor device 216.

As described above, the chassis 102 includes a cover 120. The cover 120 extends across the opening formed by the sidewalls 106 and the base 104, and is movable between an open position (depicted in FIG. 2) and a closed position (depicted in FIG. 1). In the open position, the computer processor device 200 may be inserted into or removed from the opening; and in the closed position, the computer processor device 200 is stably secured in the opening. In one embodiment, one side of the transparent cover 120 includes one or more hinges 122 for stably securing the hinged side of the transparent cover 120 to one of the sidewalls 106 of the chassis 102 to allow the opening and closing of the cover. It is also contemplated that the cover may slide between an open and closed position, such as by the use of slots or channels disposed on the sidewalls 106.

The cover 120 may be formed entirely from transparent material to allow the testing personnel to view the display 216. Alternatively, the cover 120 may be partially transparent, for example by including one or more windows, to allow the testing personnel to view the display 216.

The chassis 102 may also include wheels 108 disposed on each corner region of the lower surface of the chassis 102 (e.g., at the base 104) to allow the scanner device to move along the test subject 109 during testing. The wheels 108 may be magnetic for securing the scanner device 100 to a test subject during testing. In one exemplary embodiment, the chassis 102 includes a motor 110 for driving the wheels 108, and a power source 116 (e.g., a battery) that provides power to the motor 110. In an alternative exemplary embodiment, the chassis 102 is manually propelled by an operator and, thus, no motor is needed. Advantageously, the portability of the scanner device 100 is increased without the added weight of the motor 110.

The chassis 102 may further include at least one handle 126 formed on the chassis 102 (e.g., on one or more of the sidewalls 106 of the chassis 102). The handles 126 enable a tester to manually guide the scanner device 100 on the test subject 109.

In an exemplary embodiment, the scanner device 100 may further include a transceiver 124 in communication with the computer processor device 200. The transceiver 124 sends data produced from the testing and receives communications from a remote source relating to the testing. The transceiver 124 communicates with the remote source over one or more wireless networks. While the transceiver 124 is shown in FIG. 2 as being mounted to the chassis 102, it is contemplated that the transceiver 124 may instead be mounted to the computer processor device 200. For example the transceiver 124 may be a wireless local area network transceiver such as a Wi-Fi device.

As described above, the scanner device 100 is compact and self-contained, such that the chassis 102 and the computer processor device 200 form a single unit that is moved along a test subject. Thus configured, one tester alone may conduct the testing and simultaneously observe the results via a display mounted on the scanner device. In one embodiment, the computer processor device 216 is removable from the chassis 102, allowing for the use of standard tablet computers in lieu of costly, application-specific computers. In addition, magnetic wheels disposed on the scanner device, in conjunction with the compact design, prevent or reduce fatigue otherwise resulting from manipulation of bulkier scanner devices. Also, the same chassis 102 may be used to conduct different forms of metallurgical testing by simply changing the probes 118 and any required applications within the computer processor device 216.

While the invention has been described with reference to various exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A portable, self-contained scanner device for metallurgical nondestructive testing, the scanner device having:
    a chassis;
    wheels extending beneath a lower surface of the chassis;
    at least one probe fixed to the chassis;
    a computer processor device coupled to the chassis, the computer processor device including applications executable by the computer processor device for performing the metallurgical nondestructive testing on a test subject, the computer device executes the applications and causes the at least one probe to transmit a test signal into the test subject, senses a response to the test signal from the test subject, and provides a response signal to the computer processor device; and characterized by:
    the computer processor device being located within the chassis;
    a display device also located within the chassis and in communication with the computer processor device, the display device being configured to display images in response to the response signal, the images being viewable by testing personnel during operation of the scanner device; and
    the chassis, the computer processor device, and the display device move along the test subject as a single unit.

2. The scanner device of claim 1, wherein the chassis includes a base, sidewalls extending upward from the base, and an opening formed by the base and the sidewalls;
    wherein the computer processor device is disposed in the opening of the chassis.

3. The scanner device of claim 2, wherein the chassis further comprises a cover extending across the opening, the cover being movable between an open position and a closed position;
    wherein in the open position, the computer processor device may be inserted into or removed from the opening; and in the closed position, the computer processor device is secured in the opening, at least a portion of the cover is transparent to allow the testing personnel to view the display device when the cover is in the closed position.

4. The scanner device of claim 1, further comprising:
    an interface connector connected to the chassis, the interface connector communicatively coupled to the at least one probe; and
    a communications port on the computer processor device, the communications port being coupled to the interface connector;
    wherein the command from the at least one application is transmitted via the communications port and the interface connector.

5. The scanner device of claim 1, wherein the applications include:
    a data acquisition component receiving response signals resulting from test signal emission by the at least one probe;
    an encoder for determining a position of the scanner device on the test subject, and defining a position location at which the response signals are acquired;
    a data acquisition component for processing the response signals; and
    an imaging component for presenting processed response signals on the display device.

6. The scanner device of claim 1, wherein the chassis further comprises posts for supporting the at least one probe such that the at least one probe is removable from the posts to allow the at least one probe to be replaced with different probes.

7. The scanner device of claim 1, wherein the chassis further comprises at least one handle formed on the chassis to allow the testing personnel to manually guide the scanner device on the test subject.

8. The scanner device of claim 1, further comprising a transceiver in communication with the computer processor device, the transceiver operable for sending data produced from the metallurgical nondestructive testing and receiving communications from a remote source.

9. The scanner device of claim 1, wherein the computer processor device is a tablet computer having a display device disposed thereon and facing outwardly and in view of the testing personnel.

10. The scanner device of claim 1, further comprising a second display device communicatively coupled to the computer processor device, the second display device comprising eyewear worn by the tester, the eyewear receiving the images and displaying the images to the tester.

11. The scanner device of claim 1, wherein the wheels comprise magnetic wheels disposed proximate corner regions of the lower surface of the chassis for securing the scanner device on the test subject during testing.

12. The scanner device of claim 1, further comprising:
a motor for driving the wheels; and
a power source that provides power to the motor.

13. A chassis for a metallurgical nondestructive scanner device, comprising:
a base, sidewalls extending upward from the base, and an opening formed by the base and the sidewalls;
wheels extending beneath the base of the chassis;
at least one nondestructive testing probe fixed to the chassis characterized by:
the base being sized and shaped to receive and hold a computer processor device having a touch-sensitive screen that is visible and accessible when the scanner device is in operation; and
an interface connector attached to the chassis, the interface connector communicatively coupled to the at least one probe, the interface connector being configured to connect to a communications port of the computer processor device.

14. The chassis of claim 13, further comprising a cover extending across the opening in the chassis, the cover being movable between an open position and a closed position;
wherein in the open position, the computer processor device may be inserted into or removed from the opening; and in the closed position, the computer processor device is secured in the opening, at least a portion of the cover is transparent to allow the testing personnel to view the display device when the cover is in the closed position.

15. The chassis of claim 13, further comprising posts attached to the chassis for coupling the at least one probe to the chassis, such that the at least one probe is removable from the posts to allow the at least one probe to be replaced with different probes.

16. The chassis of claim 13, further comprising at least one handle formed on the chassis to allow the testing personnel to manually guide the scanner device on the test subject.

17. The chassis of claim 13, further comprising a transceiver operable for sending data produced from the metallurgical nondestructive testing and receiving communications from a remote source.

18. The chassis of claim 13, wherein the wheels comprise magnetic wheels disposed proximate corner regions of the lower surface of the chassis for securing the chassis on the test subject during testing.

19. The chassis of claim 13, further comprising:
a motor for driving the wheels; and
a power source that provides power to the motor.

* * * * *